United States Patent [19]

Samain et al.

[11] Patent Number: 5,685,882
[45] Date of Patent: Nov. 11, 1997

[54] USE OF GUAR GUM IN NON-RINSED COMPOSITIONS FOR THE DYEING OF KERATIN FIBERS

[75] Inventors: Henri Samain, Bievres; Marie-Pascale Audousset, Asnieres, both of France

[73] Assignee: L'Oreal, Paris, France

[21] Appl. No.: 505,532

[22] Filed: Jul. 21, 1995

[30] Foreign Application Priority Data

Jul. 22, 1994 [FR] France ................................. 94 09120

[51] Int. Cl.$^6$ ..................................................... A61K 7/13
[52] U.S. Cl. .................... 8/408; 8/405; 8/406; 8/410; 8/411; 8/412; 8/423; 8/637.1; 424/70.6
[58] Field of Search .............................. 8/404, 405, 406, 8/411, 412, 410, 414, 416, 421, 423, 435, 637.1; 424/70.6

[56] References Cited

U.S. PATENT DOCUMENTS

| | | | |
|---|---|---|---|
| 3,589,578 | 6/1971 | Kamphausen et al. | 226/40 |
| 3,912,446 | 10/1975 | Zviak et al. | 8/431 |
| 3,920,384 | 11/1975 | Feinland et al. | 8/431 |
| 3,989,447 | 11/1976 | Kalopissis et al. | 8/421 |
| 4,031,307 | 6/1977 | DeMartino et al. | 536/114 |
| 4,054,413 | 10/1977 | Feinland et al. | 8/410 |
| 4,297,098 | 10/1981 | Dasher et al. | 8/421 |
| 4,668,237 | 5/1987 | Feinland et al. | 8/424 |
| 4,690,685 | 9/1987 | Grollier et al. | 8/407 |
| 4,725,283 | 2/1988 | Cotteret et al. | 8/407 |
| 4,750,908 | 6/1988 | Rossenbaum et al. | 8/429 |
| 4,781,723 | 11/1988 | Gross et al. | 8/429 |
| 4,820,308 | 4/1989 | Madrange et al. | 8/405 |
| 4,885,006 | 12/1989 | Grollier et al. | 8/423 |
| 5,051,251 | 9/1991 | Morita et al. | 424/70 |
| 5,126,126 | 6/1992 | Varaprath et al. | 424/71 |
| 5,254,333 | 10/1993 | Kajino et al. | 8/429 |
| 5,281,240 | 1/1994 | McGee | 8/405 |
| 5,332,581 | 7/1994 | Yoshihara et al. | 8/429 |
| 5,489,431 | 2/1996 | Ascione et al. | 424/401 |

FOREIGN PATENT DOCUMENTS

| | | |
|---|---|---|
| 1188990 | 6/1985 | Canada . |
| 0 072 298 | 6/1983 | European Pat. Off. . |
| 0 424 261 | 10/1989 | European Pat. Off. . |
| 0 425 345 | 5/1991 | European Pat. Off. . |
| 0 531 738 | 3/1993 | European Pat. Off. . |
| 2 593 061 | 7/1987 | France . |
| 2 593 062 | 7/1987 | France . |
| 2 593 245 | 9/1987 | France . |
| 2 606 636 | 5/1988 | France . |
| 2 163 460 | 2/1986 | United Kingdom . |
| 2 254 341 | 10/1992 | United Kingdom . |

Primary Examiner—Paul Lieberman
Assistant Examiner—Caroline L. Dusheck
Attorney, Agent, or Firm—Finnegan, Henderson, Farabow, Garrett & Dunner, L.L.P.

[57] ABSTRACT

A method for the dyeing of keratin fibers, and in particular human keratin fibers such as the hair, by applying to the fibers non-rinsed dye compositions containing guar gum as sole thickening agent.

24 Claims, No Drawings

USE OF GUAR GUM IN NON-RINSED COMPOSITIONS FOR THE DYEING OF KERATIN FIBERS

The present invention relates to the use of guar gum in non-rinsed compositions intended for the dyeing of keratin fibers and, in particular, human keratin fibers such as hair.

Two main types of dyeing processes exist for keratin fibers: direct dyeing, using direct dyes and/or pigments, which are colored molecules that impart a temporary color to the fibers which fade away after a few shampoos, and the dyeing process known as "oxidation dyeing" using oxidation dye precursors and an oxidizing agent which imparts a persistent color to the fibers.

These two types of dyeing process require the application to the keratin fibers of compositions containing, in a support suitable for dyeing, the various direct dyes and/or pigments and/or oxidation dye precursors in the presence of an oxidation agent. These compositions are generally in the form of a thickened liquid, so as to facilitate their application to the fibers. The various thickening agents used in such compositions are generally chosen from optionally crosslinked acrylic polymers, cellulose derivatives, gum arabic, guar gum, xanthan gum, carrageenan gum, etc.

After a more or less long time of exposure of the compositions on the fibers, which allows the fibers to be impregnated with the dyes, these compositions are rinsed out in order to remove the dye support. Indeed, when this type of composition is not rinsed out, the hair is difficult to dry, and, when it is dry, it is not shiny, is coarse, sticky and furthermore strongly stains material with which it comes into contact (pillows and towels). This technique thus has the drawback of being time-consuming by requiring two nonconcurrent operations which are the exposure and the rinsing.

Moreover, European Patent Application EP-A-0,072, 298, the disclosure of which is hereby incorporated by reference, describes dye compositions containing natural direct dyes, thickened with a cationized derivative of guar gum. The application of these compositions to the hair is followed by a rinsing operation, which consequently removes most of the dyes, the result of which can only be to enhance the departure of the colors obtained.

The inventors have discovered that these various drawbacks can be overcome.

The subject of the present invention is a method for the non-rinsed, direct or oxidation dyeing of keratin fibers, and in particular of human keratin fibers such as hair. The method comprises the application to the keratin fibers of a guar gum selected from at least one nonionic guar gum and at least one guar gum modified with cationic groups, as sole thickening agent. The guar gum is in a cosmetic composition containing at least one of a direct dye, a pigment, and an oxidation dye precursor.

The use of the guar gums according to the invention makes it possible for the dye compositions not to be rinsed. The hair dries easily and, once dry, it is shiny, soft to the touch and virtually does not stain material against which it is rubbed. Moreover, the colors obtained are stronger than when a rinsing step follows the application of the dye composition. Under these conditions, it becomes possible to dye keratin fibers and in particular human keratin fibers such as the hair by employing only a single step, namely the application of the dye composition. Thus, the time spent by the operator (hairdresser or user) is greatly reduced.

The nonionic guar gums which may be used according to the invention are preferably modified with $C_1$–$C_6$ hydroxyalkyl groups.

Among the hydroxyalkyl groups there may be mentioned, by way of example, hydroxymethyl, hydroxyethyl, hydroxypropyl and hydroxybutyl groups.

These guar gums are well known in the state of the art and may, for example, be prepared by reacting corresponding alkene oxides such as, for example, propylene oxides with guar gum so as to obtain a guar gum modified with hydroxypropyl groups.

The degree of hydroxyalkylation preferably ranges from 0.4 to 1.2 and corresponds to the number of alkylene oxide molecules consumed per number of free hydroxyl functions present in the guar gum. Such nonionic guar gums optionally modified with hydroxyalkyl groups are, for example, sold under the trade names JAGUAR HP8, JAGUAR HP60 and JAGUAR HP120 by the company Mayhall.

The guar gums modified with cationic groups which may more particularly be used according to the invention are guar gums containing trialkylammonium cationic groups. Preferably, 2 to 30% in numerical terms of the hydroxyl functions of these guar gums bear trialkylammonium cationic groups. Even more preferably, 5 to 20% in numerical terms of the hydroxyl functions of these guar gums are branched with trialkylammonium cationic groups.

Among these trialkylammonium groups, there may most particularly be mentioned the trimethylammonium and triethylammonium groups.

Even more preferably, these groups represent from 5 to 20% by weight relative to the total weight of the modified guar gum.

According to the invention, a guar gum modified with 2,3-epoxypropyltrimethylammonium chloride is preferably used.

These guar gums modified with cationic groups are products that are already known per se and are, for example, described in U.S. Pat. Nos. 3,589,578 and 4,031,307, the disclosures of which are hereby incorporated by reference. Moreover, such products are sold in particular under the trade names JAGUAR C 13 S, JAGUAR C 15 and JAGUAR C 17 by the company Mayhall.

According to the invention, the nonionic guar gums and/or the guar gums modified with cationic groups are used, in general, at an amount of 0.1 to 3% by weight relative to the total weight of the dye composition and even more preferably at an amount of 0.25 to 2.5% by weight.

The direct dyes which may be used according to the invention are chosen from direct dyes conventionally employed for the direct dyeing of keratin fibers. Among these there may be mentioned, by way of example, the nitro derivatives of the benzene series, azo dyes, anthraquinone dyes, indamines, indoanilines and indophenols, acidic dyes such as those catalogued in the Color Index 3rd edition, the disclosure of which is incorporated by reference, and natural dyes such as Lawsone. These direct dyes may optionally bear sulfonic groups or cationic groups so as to improve their solubility in the dyeing medium used.

The pigments which may be used according to the invention may be chosen from the inorganic or organic pigments conventionally used in cosmetics.

Among the inorganic pigments there may, by way of example, be mentioned titanium dioxide (rutile or anatase) optionally surface-treated and catalogued in the Color Index under the reference code CI 77891; black, yellow, red and brown iron oxides, catalogued under the reference codes CI 77499, 77492 and 77491: manganese violet (CI 77742); ultramarine blue (CI 77007); hydrated chromium oxide (CI 77289); ferric blue (CI 77510).

Among the organic pigments there may, by way of example, be mentioned the pigment yellow 3 sold in particular under the trade name JAUNE COVANOR W 1603 by the company Wacker (CI 11710), D & C red No. 19 (CI 45170), D & C red No. 9 (CI 15585), D & C red No. 21 (CI 45380), D & C orange No. 4 (15510), D & C orange No. 5 (CI 45370), D & C red No. 27 (CI 45410), D & C red No. 13 (CI 15630), D & C red No. 7 (CI 15850-1), D & C red No. 6 (CI 15850-2), D & C yellow No. 5 (CI 19140), D & C red No. 36 (CI 12085), D & C orange No. 10 (CI 45425), D & C yellow No. 6 (CI 15985), D & C red No. 30 (CI 73360), D & C red No. 3 (CI 45430), carbon black (CI 77266), and the lakes based on cochineal carmine (CI 75470).

It is also possible to use pearlescent pigments which may in particular be chosen from white pearlescent pigments such as mica coated with titanium oxide, bismuth oxide; colored pearlescent pigments such as titanium mica with iron oxides, titanium mica with ferric blue or chromium oxide, titanium mica with an organic pigment of precipitated type, as well as those based on bismuth oxychloride.

The oxidation dye precursors which may be used according to the invention in the compositions intended for oxidation dyeing are known per se. Reference may be made more particularly to Zviak, Sciences des traitements capillaires [Hair treatment sciences] 1988, pages 235 to 287, the disclosure of which is incorporated by reference herein. These are more particularly diamines or aminophenols containing amino and hydroxyl functional groups in the para or ortho position. These oxidation dye precursors, also known as oxidation bases, are colorless or weakly colored compounds which, once mixed with oxidizing products, at the time of use, may give rise via an oxidative condensation process to colored compounds and dyes.

It is also known that the shades obtained with these oxidation bases may be varied by combining them with dye modifiers or couplers, chosen in particular from aromatic meta-diamines, meta-aminophenols and meta-diphenols.

The dye compositions may also contain indole precursors generating pigments of melanin-type under the action of an oxidizing agent. These indole precursors are more particularly described in French patents and patent applications FR-A-2,593,061, 2,593,062, 2,595,245, 2,606,636 and 2,636,237 and European patent applications EP-A-425,345 and EP-A-424,261, the disclosures of all of which are hereby incorporated by reference. The preferred indole precursors are chosen from 5,6-dihydroxyindole and derivatives thereof and 6- and 7-monohydroxyindoles.

The appropriate dyeing medium is generally an aqueous medium consisting of water or a mixture of water and an organic solvent which is used to solubilize the compounds which would not be sufficiently soluble in water.

Among these solvents there may, by way of example, be mentioned $C_1$–$C_4$ lower alkanols such as ethanol and isopropanol; glycerol; glycols and glycol ethers such as 2-butoxyethanol, propylene glycol, diethylene glycol monoethyl ether and diethylene glycol monomethyl ether; aromatic alcohols such as benzyl alcohol or phenoxyethanol; similar products and mixtures thereof. According to the invention, C–$C_4$ lower alcohols, and most particularly ethanol, are preferably used.

When they are present, the solvents preferably represent 1 to 50% by weight of the total weight of the dye composition and even more preferably from 5 to 40% by weight.

The pH of the composition applied to the hair is preferably from 3 to 11. It is adjusted to the desired value using basifying agents usually used in the dyeing of keratin fibers, such as aqueous ammonia, alkali metal carbonates, alkanolamines such as, for example, mono-, di- and triethanolamines and derivatives thereof, and sodium hydroxide or potassium hydroxide, or using conventional acidifying agents such as inorganic or organic acids like, for example, hydrochloric acid, tartaric acid, citric acid, lactic acid and orthophosphoric acid.

The dye composition may additionally contain at least one adjuvant commonly used in the dyeing of keratin fibers, on condition that this adjuvant does not modify the consistency of the dye composition and does not result in hair which feels unpleasant.

Among these adjuvants, there may be mentioned preserving agents, sequestering agents, antioxidants, fragrances, nonionic surfactants, sunscreens, etc.

The dye composition thickened by the guar gum or gums used according to the invention is in the form of gel of thicker or thinner consistency.

Another subject of the invention is a method for dyeing keratin fibers and in particular human keratin fibers such as the hair, wherein a dye composition is applied to these fibers, this dye composition containing at least one of a direct dye, a pigment and an oxidation dye precursor, and at least one guar gum selected from a nonionic guar gum and a guar gum modified with cationic groups as defined above, then the fibers are allowed to dry or are dried using a hair-drier without rinsing them. When the fibers are dry, they may be combed or run through by hand in order to free them of knots.

When the dye compositions are used for oxidation dyeing, they are mixed at the time of use with a composition containing, in a medium which is suitable for dyeing, at east one oxidizing agent.

The oxidizing agent is chosen from oxidizing agents conventionally used in oxidation dyeing and preferably from hydrogen peroxide, urea peroxide, alkali metal bromates, and persalts such as perborates and persulfates. Hydrogen peroxide is particularly preferred.

The composition containing the oxidizing agent may also be thickened and, in this case, it does not contain any thickening agent other than the guar gums as defined above.

The pH of the oxidizing composition is such that, after mixing with the dye composition, the pH of the resultant composition applied to the keratin fibers is preferably from 3 to 11. It is adjusted to the desired value using acidifying agents or optionally basifying agents that are well known in the state of the art, such as described above.

The mixture of the dye composition and the oxidizing composition is then applied to the keratin fibers under the same conditions as above.

The examples which follow are intended to illustrate the invention without, however, limiting the scope thereof.

EXAMPLE 1: USE IN DIRECT DYEING

Dye compositions 1 and 2 below were prepared:

| Composition 1, comparative | |
|---|---|
| Lawsone | 0.5 g |
| Crosslinked acrylic acid polymer sold under the trade name CARBOPOL 934 by the company Goodrich | 1 g |
| Ethanol | 50 g |
| Demineralized water | q.s. 100 g |
| Composition 2, inventive | |
| Lawsone | 0.5 g |
| Guar gum modified with cationic groups, sold under the trade name | 1 g |

| JAGUAR C 13 S by the company Mayhall | |
|---|---|
| Ethanol | 50 g |
| Demineralized water | q.s. 100 g |

These compositions were applied to locks of European hair, which had been washed beforehand with shampoo, in an amount of about 1 g of composition per gram of hair. The hair was allowed to dry naturally and the knots were then removed with a comb.

The hair dyed with composition 1, using a thickening agent not forming part of the invention, was difficult to dry and, after waiting until it was dry, it had an unpleasant and unacceptable feel. Furthermore, the hair stained paper on which it was rubbed.

In contrast, the hair dyed with composition 2, using a guar gum modified with cationic groups according to the invention, dried easily, and it had an intense color and a natural and pleasant feel. When passed over a sheet of paper, the lock left virtually no trace.

EXAMPLE 2

The following dye composition was prepared:

| Acid black 1 (reference No. CI 20470 in the Color Index 3rd edition), sold by the company Zeneca Colors | 0.072 g |
|---|---|
| Acid violet 43 (reference No. CI 60 730 in the Color Index 3rd edition, sold by the company Tricon Colors | 0.092 g |
| Orange Sultacide JR Extra, sold by the company Zeneca Colors | 0.256 g |
| Guar gum modified with cationic groups, sold under the trade name JAGUAR C 13 S by the company Mayhall | 1 g |
| Citric acid | q.s. pH 2.8 |
| Demineralized water | q.s. 100 g |

This composition was applied to wet, natural, grey hair containing 90% white hairs.

The hair was allowed to dry and was then combed.

The hair was dyed light brown and had a natural and pleasant feel.

EXAMPLE 3

The following dye composition was prepared:

| N1, N4, N4-tris(6-hydroxyethyl)-1,4-diamino-2-nitrobenzene (reference No. HC BLUE 2 in the Color Index 3rd edition), sold by the company James Robinson | 0.7 g |
|---|---|
| 1-methylamino-2-nitro-5-6,y-di-hydroxypropyloxybenzene | 0.3 g |
| Guar gum modified with cationic groups, sold under the trade name JAGUAR C 13 S by the company Mayhall | 2 g |
| Ethanol | 5 g |
| Demineralized water (intrinsic pH: 7.5) | q.s. 100 g |

This composition was applied to locks of wet, natural grey hair containing 90% white hairs.

The hair was allowed to dry and was then combed.

The hair was dyed in a light ash shade and had a natural and pleasant feel.

EXAMPLE 4

The following dye composition was prepared:

| N1, N4, N4-tris((3-hydroxyethyl)-1,4-diamino-2-nitrobenzene (reference No. HC BLU-P, 2 in the Color Index 3rd edition), sold by the company James Robinson | 1.4 g |
|---|---|
| 1-methylamino-2-nitro-5-6,y-di-hydroxypropyloxybenzene | 0.6 g |
| Guar gum modified with cationic groups, sold under the trade name JAGUAR C 13 S by the company Mayhall | 2 g |
| Ethanol | 15 g |
| Demineralized water | q.s 100 g |

About 4 g of the above dye composition were spread onto a head of blonde hair which had been washed beforehand.

The hair was dried with a hair-drier.

The hair was dyed an ashen light chestnut and had a natural and pleasant feel.

EXAMPLE 5: USE IN OXIDATION DYEING

Dye compositions 1 and 2 below were prepared:

| Composition 1, comparative: | |
|---|---|
| Para-phenylenediamine | 0.15 g |
| 2,4-Diamino-1-6-hydroxyethyloxy-benzene dihydrochloride | 0.08 g |
| 1-Hydroxy-3-aminobenzene | 0.15 g |
| Crosslinked acrylic acid polymer sold under the trade name CARBOPOL 934 by the company Goodrich | 1 g |
| Ethanol | 30 g |
| Monoethanolamine | 0.2 |
| Demineralized water | q.s. 100 g |
| Composition 2, inventive: | |
| Para-phenylenediamine | 0.15 g |
| 2,4-Diamino-1-6-hydroxyethyloxy-benzene dihydrochloride | 0.08 g |
| 1-Hydroxy-3-aminobenzene | 0.15 g |
| Guar gum modified with cationic groups, sold under the trade name JAGUAR C 13 S by the company Mayhall | 1 g |
| Ethanol | 30 g |
| Monoethanolamine | 0.2 g |
| Demineralized water | q.s. 100 g |

At the time of use, dye composition 1 was mixed with an equal amount of the following oxidizing composition:

| Aqueous hydrogen peroxide solution | 10 volumes |
|---|---|
| Orthophosphoric acid | q.s. pH 3 |
| Crosslinked acrylic acid polymer sold under the trade name CARBOPOL 934 by the company Goodrich | 1 q |
| Demineralized water | q.s. 100 g |

At the time of use, dye composition 2 was mixed with an equal amount of the following oxidizing composition:

| Aqueous hydrogen peroxide solution | 10 volumes |
|---|---|
| Orthophosphoric acid | q.s. pH 3 |
| Guar gum modified with cationic groups, sold under the trade name | 1 g |

| | |
|---|---|
| JAGUAR c 13 S by the company Mayhall | |
| Demineralized water | q.s. 100 g |

The pH of the resulting compositions applied to the hair was 6.5. These mixtures were applied to locks of European hair, which had been washed beforehand with shampoo, in an amount of 1 g of composition per gram of hair. The hair was allowed to dry naturally and the knots were then removed therefrom with a comb.

The hair dyed with composition 1, using a thickening agent not forming part of the invention, was difficult to dry and, once dry, had an unpleasant and unacceptable feel.

Only by rinsing was it possible to obtain a natural feel. Furthermore, the lock stained paper on which it was rubbed.

In contrast, the hair dyed with composition 2, using a guar gum modified with cationic groups according to the invention, dried easily and had an intense color. It felt natural and pleasant. The lock left no trace when passed over a sheet of paper.

EXAMPLE 6

The following dye composition was prepared:

| | |
|---|---|
| Para-phenylenediamine | 0.35 g |
| 2,4-Diamino-1-(6-hydroxyethyloxy-benzene dihydrochloride | 0.2 g |
| 3-Aminophenol | 0.35 g |
| Guar gum modified with hydroxypropyl groups, sold under the trade name JAGUAR HP60 by the company Mayhall | 1.2 |
| Ethanol | 25 g |
| Monoethanolamine | 1 g |
| Demineralized water | q.s. 100 g |

At the time of use, the above dye composition was mixed with an equal amount of water.

The hair was dyed mid-grey and had a natural and pleasant feel.

EXAMPLE 7

The following dye composition was prepared:

| | |
|---|---|
| Jaune Covanor W1603 (reference No. pigment yellow 3 in the Color Index 3rd edition), sold by the company Wacker | 1 g |
| Guar gum modified with cationic groups, sold under the trade name JAGUAR C 13 S by the company Mayhall | 1 g |
| Ethanol | 20 g |
| Demineralized water (intrinsic pH: 6.2) | q.s. 100 g |

This composition was applied to natural grey hair containing 90% white hairs. The hair was allowed to dry and was then combed.

The hair was dyed yellow and had a natural and pleasant feel.

What is claimed is:

1. A method for dyeing of keratin fibers, said method comprising the steps of:
   applying to said keratin fibers at least one guar gum, said guar gum being a nonionic guar gum modified with at least one $C_1$–$C_6$ hydroxyalkyl group or a guar gum modified with at least one cationic group,
   wherein said guar gum is applied in a cosmetic composition additionally containing at least one of a pigment and an indole precursor, further wherein said method includes no rinsing step, and further wherein said guar gum is the sole thickening agent in said composition; and
   allowing the fibers to dry or drying them with a hair-drier, without rinsing said fibers.

2. The method of claim 1, wherein said keratin fibers. are human keratin fibers.

3. The method of claim 2, wherein said human keratin fibers are human hair.

4. The method of claim 1, wherein said at least one hydroxyalkyl group is a hydroxymethyl, a hydroxyethyl, a hydroxypropyl or a hydroxybutyl group.

5. The method of claim 1, wherein said nonionic guar gum has a degree of hydroxyalkylation ranging from 0.4 to 1.2.

6. The method of claim 1, wherein said at least one cationic group of the guar gum is a trialkylammonium group.

7. The method of claim 6, wherein said trialkylammonium group is a trimethylammonium or triethylammonium group.

8. The method of claim 6, wherein said at least one cationic group represents less than 30% by weight relative to the total weight of the modified guar gum.

9. The method of claim 8, wherein said at least one cationic group represents from 5 to 20% by weight relative to the total weight of the modified guar gum.

10. The method of claim 6, wherein said guar gum is modified with 2,3-epoxypropyltrimethyl-ammonium chloride.

11. The method of claim 1, wherein the amount of guar gum selected from at least one of nonionic guar gum and guar gum modified with cationic groups is from 0.1 to 3% by weight relative to the total weight of said cosmetic composition.

12. The method of claim 11, wherein the amount of guar gum selected from at least one of nonionic guar gum and guar gum modified with cationic groups is from 0.25 to 2.5% by weight relative to the total weight of said cosmetic composition.

13. The method of claim 1, wherein said at least one pigment is an inorganic pigment, an organic pigment or a pearlescent pigment.

14. The method of claim 1, wherein said composition contains at least one indole precusor.

15. The method of claim 14, wherein said at least one indole precursor is a 5,6-dihydroxyindole, 6-monohydroxyindole or a 7-monohydroxyindole.

16. The method of claim 1, wherein said composition contains an aqueous medium comprising water or a mixture of water and an organic solvent.

17. The method of claim 1, wherein said composition contains at least one adjuvant, said adjuvant being a preserving agent, a sequestering agent, an antioxidant, a fragrance, a nonionic surfactant or a sunscreen.

18. A method for dyeing keratin fibers comprising the steps of:
    mixing a dye composition with an oxidizing composition to form a mixture, said dye composition containing at least one oxidation dye precursor and at least one guar gum,
    wherein the guar gum is a nonionic guar gum modified with at least one $C_1$–$C_6$ hydroxyalkyl group or a guar gum modified with at least one cationic group, further wherein said method includes no rinsing step, and further wherein said guar gum is the sole thickening agent in said composition;
    applying said mixture to said fibers; and allowing the fibers to dry or drying them with a hair-drier, without rinsing said fibers.

19. The method of claim 18, wherein said keratin fibers are human keratin fibers.

20. The method of claim 19, wherein said human keratin fibers are human hair.

21. The method of claim 18, wherein said at least one oxidation dye precursor is a para or ortho diamine or a para or ortho aminophenol.

22. The method of claim 21, wherein said composition additionally contains at least one coupler, said coupler being an aromatic meta-diamine, a meta-aminophenol or a meta-diphenol.

23. A method for dyeing keratin fibers, said method comprising the steps of:

applying to said keratin fibers a cosmetic composition which contains 0.1 to 3% by weight, relative to the total weight of the cosmetic composition, of at least one guar gum, said guar gum being a guar gum modified with at least one cationic group, wherein said cosmetic composition additionally contains at least one of a direct dye, further wherein said method includes no rinsing step, and further wherein said guar gum is the sole thickening agent in said composition; and allowing the fibers to dry or drying them with a hair-drier, without rinsing said fibers.

24. The method of claim 23, wherein said at least one direct dye is a nitro derivative of the benzene series, an azo dye, an anthraquinone dye, an indamine, an indoaniline, an indophenol, an acidic dye or a natural dye.

* * * * *